United States Patent
Lechot et al.

(10) Patent No.: US 7,780,669 B2
(45) Date of Patent: *Aug. 24, 2010

(54) REAMER SPINDLE FOR MINIMALLY INVASIVE JOINT SURGERY

(75) Inventors: André Lechot, Orvin (CH); Yves Desarzens, Corgémont (CH); Hugh Davies, Huddersfield (GB); Patrick White, West Chester, PA (US)

(73) Assignee: Greatbatch Medical S.A., Orvin (CH)

( * ) Notice: Subject to any disclaimer, the term of this patent is extended or adjusted under 35 U.S.C. 154(b) by 413 days.

This patent is subject to a terminal disclaimer.

(21) Appl. No.: 11/935,198

(22) Filed: Nov. 5, 2007

(65) Prior Publication Data

US 2008/0065081 A1 Mar. 13, 2008

Related U.S. Application Data

(63) Continuation of application No. 11/123,932, filed on May 5, 2005, now Pat. No. 7,637,909, which is a continuation of application No. PCT/IB03/01725, filed on Apr. 28, 2003.

(60) Provisional application No. 60/376,479, filed on Apr. 30, 2002, provisional application No. 60/384,186, filed on May 30, 2002, provisional application No. 60/459,594, filed on Apr. 2, 2003.

(51) Int. Cl.
*A61B 17/00* (2006.01)
(52) U.S. Cl. .......................... 606/80; 606/81; 606/86 R
(58) Field of Classification Search ............... 606/86 R, 606/80, 81, 79, 167, 96, 87
See application file for complete search history.

(56) References Cited

U.S. PATENT DOCUMENTS 4,305,394 A * 12/1981 Bertuch, Jr. .................. 606/91

(Continued)

FOREIGN PATENT DOCUMENTS

JP 123334 5/1993

(Continued)

OTHER PUBLICATIONS

Suggestion for interference filed in U.S. Appl. No. 11/122,092, on Feb. 24, 2006.

(Continued)

*Primary Examiner*—Pedro Philogene
(74) *Attorney, Agent, or Firm*—Michael F. Scalise

(57) ABSTRACT

An adjustable reamer spindle is provided to aid the surgeon in controlling the instrument. The reamer spindle is easily disassembled for cleaning. The spindle has a repositionable handle, a locking ring, and an elastic device. The elastic device biases against a handle locking mechanism that locks the repositionable handle at angular positions about an axis of the spindle. The elastic device further biases a locking ring into a locked position. The locking ring aids in holding the reamer spindle together. Removal of the locking ring against an elastic bias of the elastic means unfastens an end of the assembly in order to facilitate disassembly and/or cleaning. Adjustment of the position of the handle about the spindle enables the palm/grip of each hand to be changed in order to provide maximum control in different orientations. The adjustment is desirable in order to accommodate operating on the left or right side of the patient, standing behind or in-front of the patient, or the use of a different surgical approach. Further, adjustment is important to accommodate the differing needs of surgeons who are naturally left or right handed.

17 Claims, 12 Drawing Sheets

U.S. PATENT DOCUMENTS

| | | | |
|---|---|---|---|
| 4,528,980 A | 7/1985 | Kenna | |
| 5,171,312 A | 12/1992 | Salyer | |
| 5,176,711 A | 1/1993 | Grimes | |
| 5,474,560 A | 12/1995 | Rohr, Jr. | |
| 5,925,077 A * | 7/1999 | Williamson et al. | 623/22.34 |
| 5,951,561 A * | 9/1999 | Pepper et al. | 606/80 |
| 6,174,313 B1 | 1/2001 | Bonutti | |
| 6,312,438 B1 | 11/2001 | Adams | |
| 6,436,107 B1 * | 8/2002 | Wang et al. | 606/139 |
| 6,451,058 B2 | 9/2002 | Tuke | |
| 6,475,221 B1 | 11/2002 | White | |
| 0,300,557 A1 | 8/2003 | Chana, Gursharan | |
| 6,676,706 B1 | 1/2004 | Mears | |
| 6,854,742 B2 * | 2/2005 | Salyer et al. | 279/93 |
| 7,008,430 B2 | 3/2006 | Dong et al. | |
| 2002/0004660 A1 | 1/2002 | Henniges et al. | |
| 2003/0050645 A1 | 3/2003 | Myers et al. | |
| 2003/0130741 A1 | 7/2003 | McMinn | |
| 2004/0087958 A1 | 5/2004 | Myers et al. | |

FOREIGN PATENT DOCUMENTS

| | | |
|---|---|---|
| JP | 05123334 | 5/1993 |
| WO | 03065906 A3 | 8/2001 |
| WO | 03065906 A2 | 8/2003 |
| WO | 03092513 | 11/2003 |

OTHER PUBLICATIONS

Suggestion for interference filed in U.S. Appl. No. 11/122,092, on Mar. 10, 2006.
Office action dated Jul. 9, 2008 in U.S. Appl. No. 10/503,788.
Office action dated Mar. 12, 2009 in U.S. Appl. No. 10/503,788.
Office action dated Dec. 17, 2007 in U.S. Appl. No. 10/503,788.

* cited by examiner

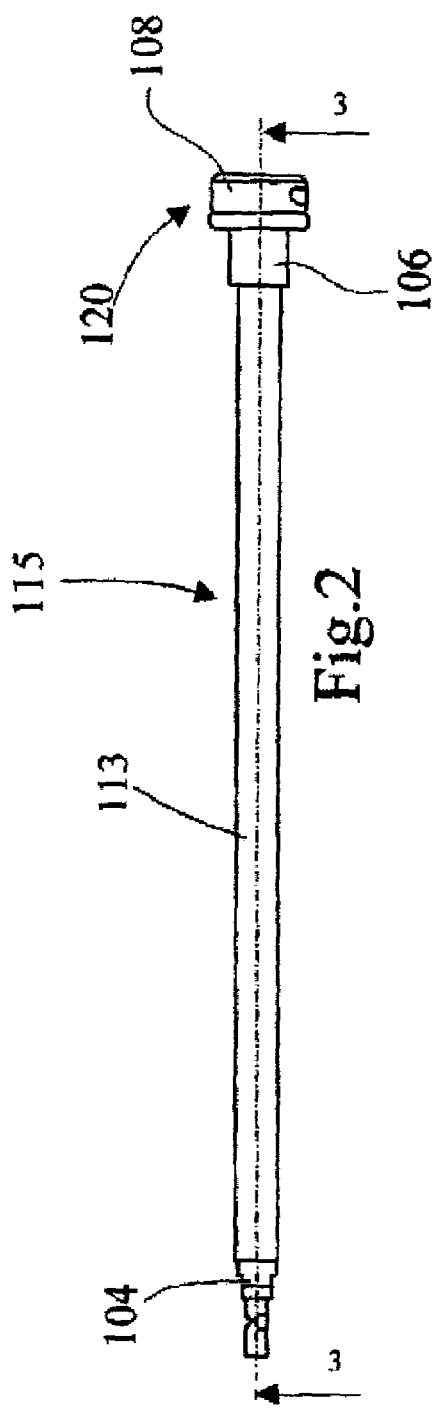
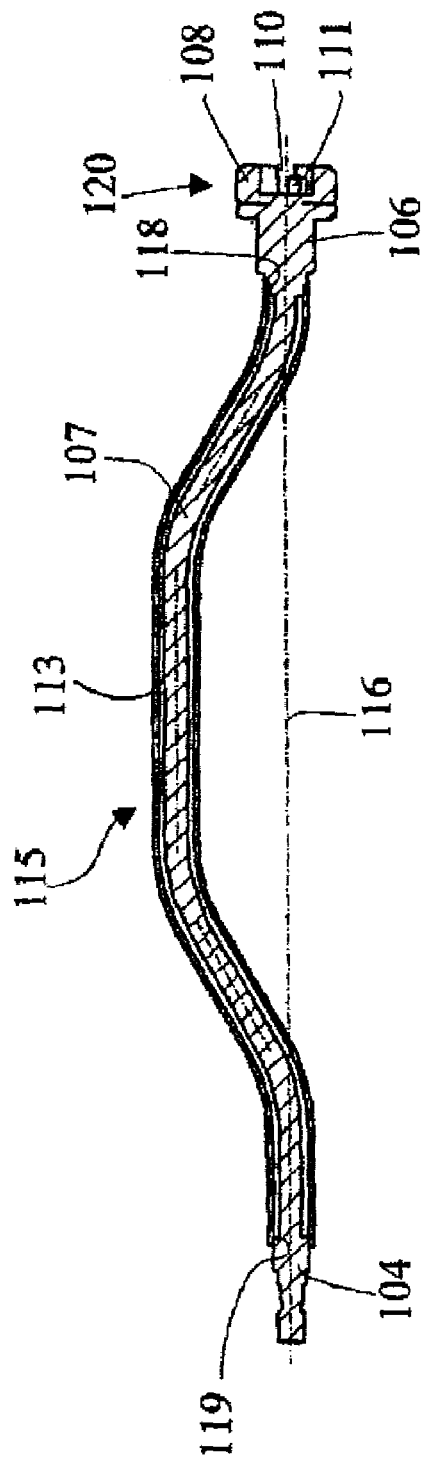

REAMER SPINDLE FOR MINIMALLY INVASIVE JOINT SURGERY

CROSS REFERENCE TO RELATED APPLICATIONS

This application is a continuation of U.S. Ser. No. 11/123,932 filed on May 5, 2005 now U.S. Pat. No. 7,637,909 which is a continuation of U.S. Ser. No. 11/123,932 which is a continuation of prior PCT application no. PCT/IB03/01725 filed 28 Apr. 2003, and claims priority thereto as well as to U.S. Provisional Applications 60/376,479, filed 30 Apr. 2002; 60/384,186, filed 30 May 2002; and 60/459,594, filed 2 Apr. 2003, the contents of all of which are incorporated herein by reference and relied upon.

BACKGROUND OF THE INVENTION

This invention relates to handles for reamers, and, more particularly, to adjustable handles for acetabular reamers that can be easily sterilized.

Complicated mechanical devices have crevasses and recesses that are difficult, if not almost impossible, to clean with ease. Devices that are not properly cleaned and sterilized contribute to the risk of disease transfer from patient to patient following the emergence of certain "prions" that are not killed by normal hospital sterilisation and need to be physically removed by washing/rinsing.

In GB PCT application no GB0202934A to Chana, entitled, Improved Surgical Devices and Methods of Use, the contents of which are incorporated by reference hereto, several reamer spindle designs are discussed. However, none includes a handle having the ability to be angularly repositioned about the axis of the housing and none uses a single spring to both lock the angularly repositionable handle in place and to lock the two housing portions in place.

What is needed therefore is a reamer spindle that is easily adjustable, disassemblable, and cleanable and which includes an easily repositionable handle using a mechanism requiring few components.

SUMMARY OF THE INVENTION

An adjustable reamer spindle is provided to aid the surgeon in controlling the instrument. Adjustment of the position of the handle axis of the spindle enables the axis through the palm/grip of each hand to change in order to provide maximum control in different orientations. The adjustment is desirable in order to accommodate operating on the left or right side of the patient, standing behind or in-front of the patient, or the use of a different surgical approach. Further, adjustment is important to accommodate the differing needs of surgeons who are naturally left or right handed. Thus, the comfort for holding and using the instrument is enhanced through adjustment.

In an objective of the invention, the handle can be easily cleaned, in that the design access to all surfaces such that they can be cleaned (i.e., one part covering another can be moved or removed to expose all surfaces). Further, the design enables the reduction in number of small radius internal corners, crevasses and small gaps and the absence of blind holes.

In another objective, a reamer handle is provided that is easy to disassemble and for which the disassembly is easy to learn.

In another object, the invention minimises the number of pieces and thus the risk that any individual part might be lost.

BRIEF DESCRIPTION OF DRAWINGS

The attached drawings represent, by way of example, different embodiments of the subject of the invention.

FIG. 2 is a top view of the reamer spindle of the present invention.

FIG. 3 is a section view taken along line 3-3 shown in FIG. 2.

DETAILED DESCRIPTION

Figure 1:
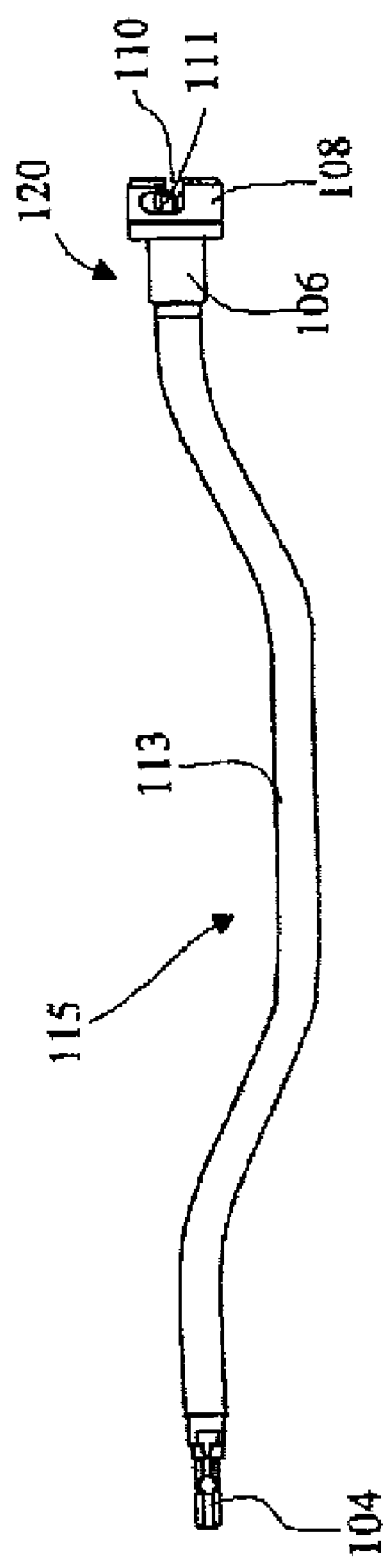
FIG. 1 is a side view of the reamer spindle of the present invention.
Figure 4:
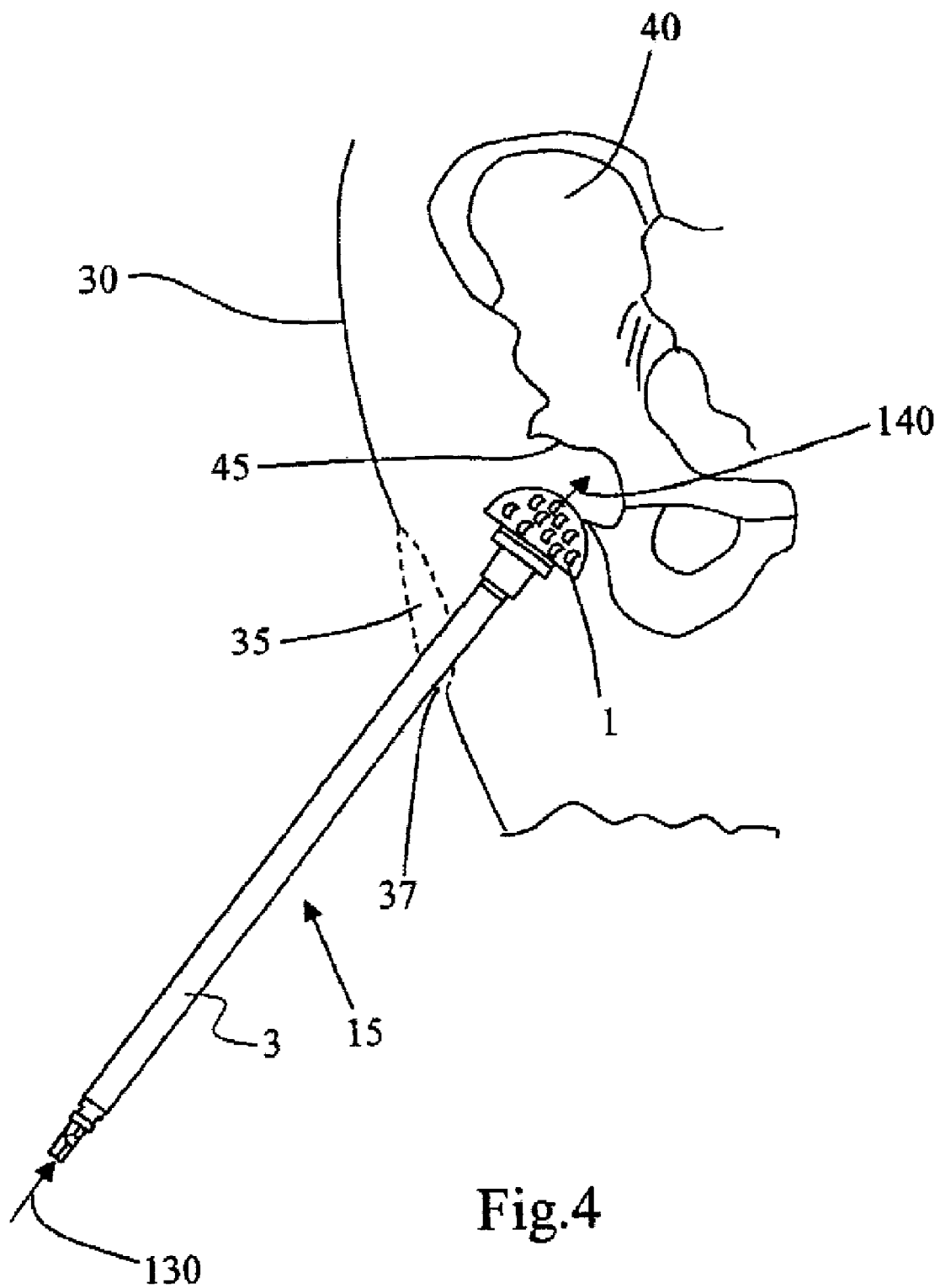
FIG. 4 is a plan view showing a traditional reamer spindle of the prior art being used in a minimally invasive approach for reaming the acetabular socket.
Figure 5:
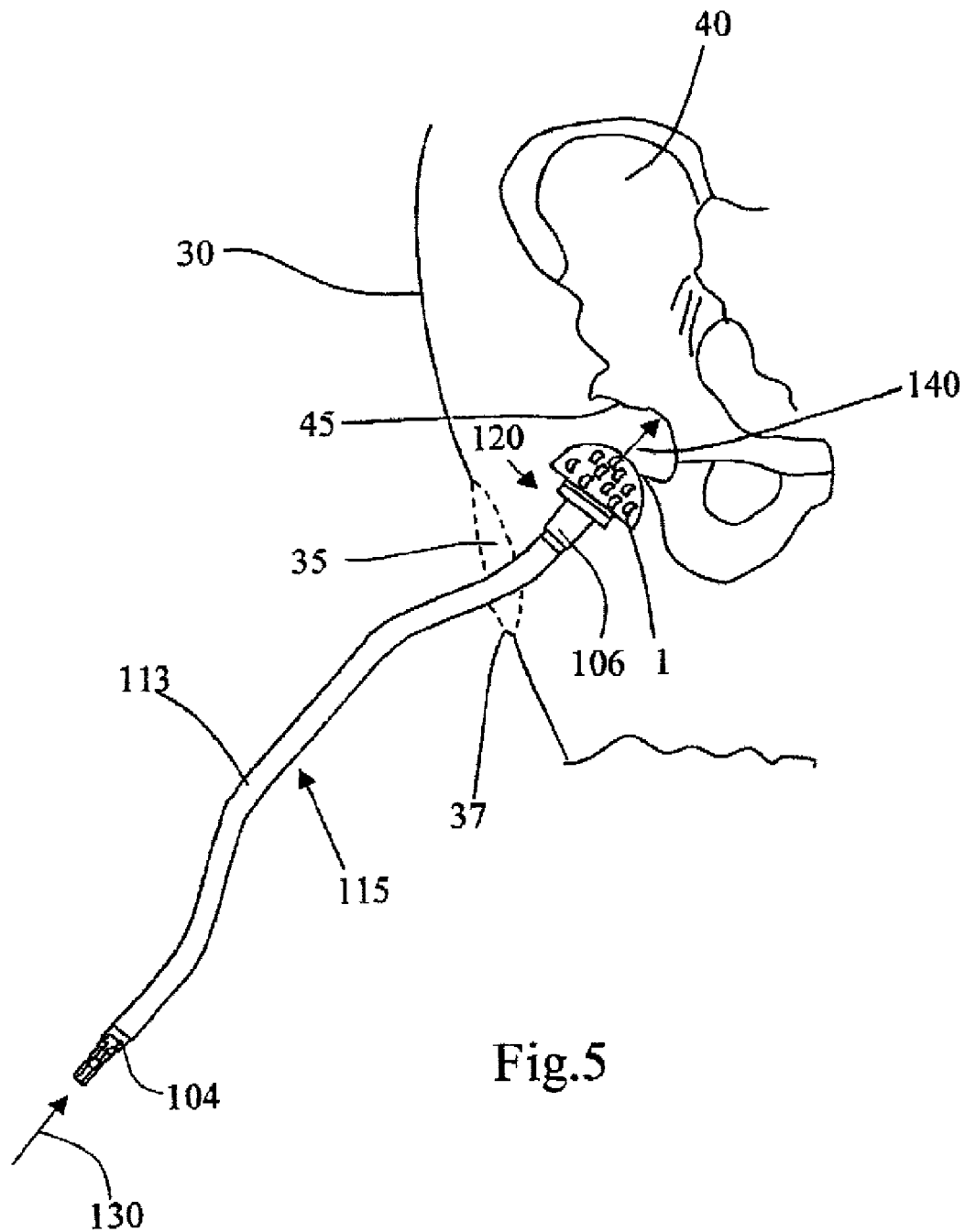
FIG. 5 is a plan view showing the reamer spindle of the present invention being used in a minimally invasive approach for reaming the acetabular socket.

The reamer spindle 115 shown in FIGS. 1-3, and 5 consists of a drive fitting 104, which is adapted to be joined to a rotary power source used to drive the shaft 107 of the reamer spindle 115. The shaft 107 is mounted to a reamer holding mechanism 120. The reamer holding mechanism 120 can be selected from a variety of mechanisms useful for capturing and holding a surgical reamer 1 during an orthopedic surgical procedure. It is clear that many different mechanisms exist which would be useful for this task, however the present inventors have selected the preferred bayonet style mechanism 120 for purpose of example. The reamer holding mechanism 120 comprises a slide 106 carrying a pin component 111 of the reamer holding mechanism 120. The pin 111 works cooperatively with the catch 110 located in the head 108 to form the bayonet for capturing different size reamers 1 while allowing their easy release for size interchangeability and cleaning. The reamers 1 selected for use with the reamer spindle 115 can be shaped and sized for cutting different osseous sites within the body. It is widely known that reamers can be designed to cut the patella in a knee or the glenoid in a shoulder or the socket 45 in an acetabulum 40 as shown in FIGS. 4-5.

Referring to FIGS. 4-5, the reamer spindle 115 of the present invention and the spindle 15 of the prior art invention are shown passing through a miniature incision 35 in the patient's skin 30. In FIG. 4, the reamer spindle 15 is shown approaching the acetabulum 40 in a preferred orientation for reaming the socket 45. The difficulty with the prior art spindle 15 is shown as the shaft 3 impinges on the miniature incision 35 at edge of the incision 37. The current surgical protocols are being pushed to the limits and the incision sizes are being reduced in the hopes of increasing the patient's speed to recovery. In some cases surgeons are using a two-incision approach, one to reach the acetabulum and the other to reach the femur. Depending on the situation, either the one incision or the two incision technique results in less trauma to the patient, thus requiring the instruments to be flexible and more optimally designed to make up for the lack of operating space.

The reamer 115 of FIG. 5 shows a new reamer spindle 115, which has a bent housing 113 containing the drive shaft 107. The drive shaft 107 can be selected from a variety of current torque transmitting mechanisms or devices including a Nickel Titanium shaft, a flexible round or flat wire wound cable, a series of gear driven shafts, or a series of shafts interconnected by universal joints. The drive shaft 107 can also be selected from any torque transmission mechanism or device deemed appropriate for the application. The drive shaft 107 can be held to the housing 113 with an optional series of bearings 118-119 which keep the drive shafts from bearing against/riding on the inside of the housing 113 and act as a shield to protect the inner housing from blood. Other means for holding the shaft to the housing would be acceptable. The most important feature of the drive shaft 107 is that it conforms to the selected housing 113 and sufficiently supplies torque to the cutter 1.

Figure 8:
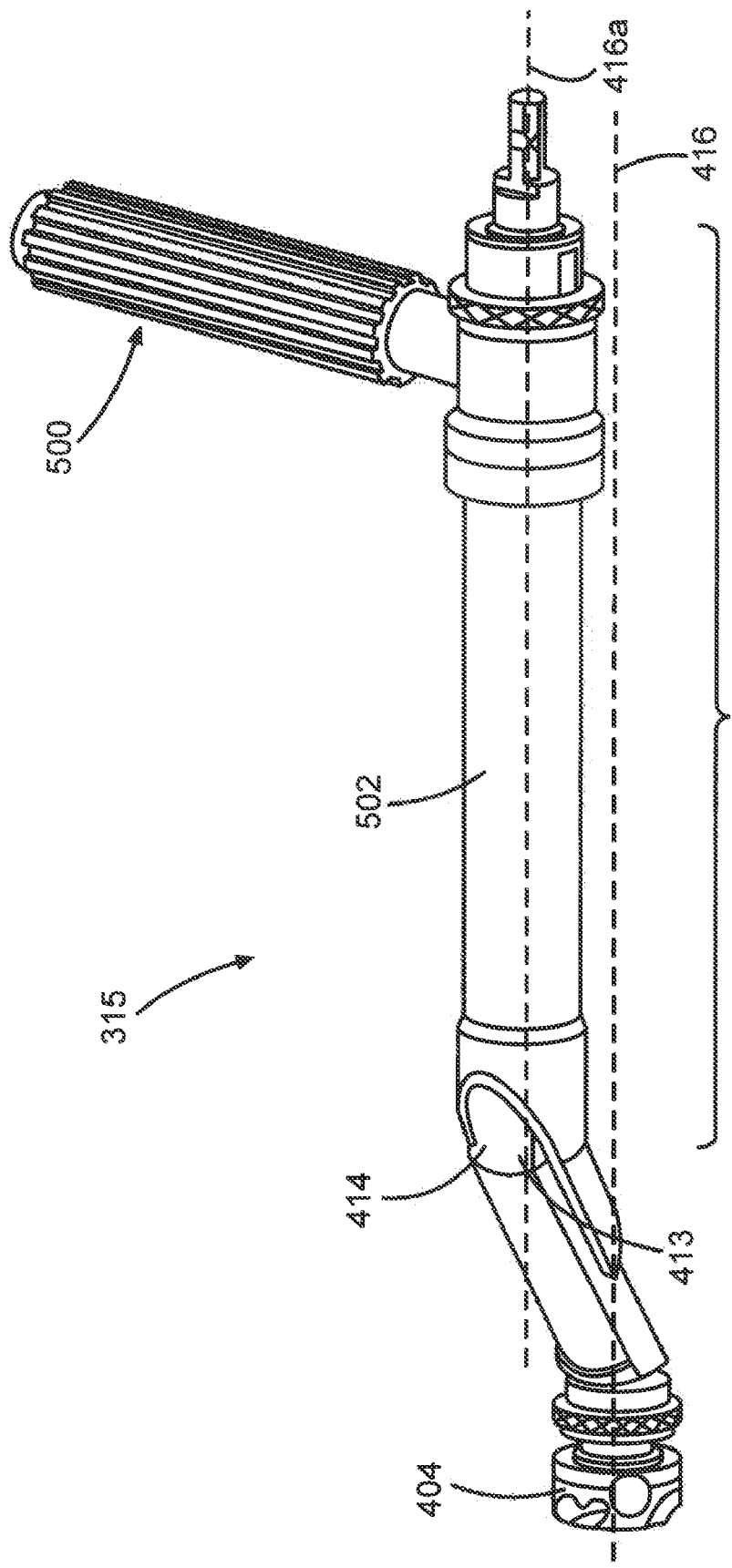
FIG. 8 is a perspective view of an alternate embodiment of the invention having a repositionable handle.

The housing 113 is formed from cannulated material and the drive end 104 is substantially collinear with the holding mechanism 120 along axis 116. Referring now to FIG. 8 et seq., alternatively, the drive end 104 could be situated along an axis parallel or offset to axis 116. The bends in the housing are optimally placed at critical locations to pass through the miniature incision without impinging on the skin 30 at location 37 while still maintaining the same surgical protocol. The drive end 104 and the holding mechanism 120 should be in line or on parallel axes so that the applied force 130 results in an axial motion 140. This allows the surgeon to maintain the existing technique because inherently reamer spindle 15 in FIG. 4 would give the same result since it has a straight drive shaft 3. Thus, the surgeon is allowed to apply a load directly along the path of reaming.

Figure 6:
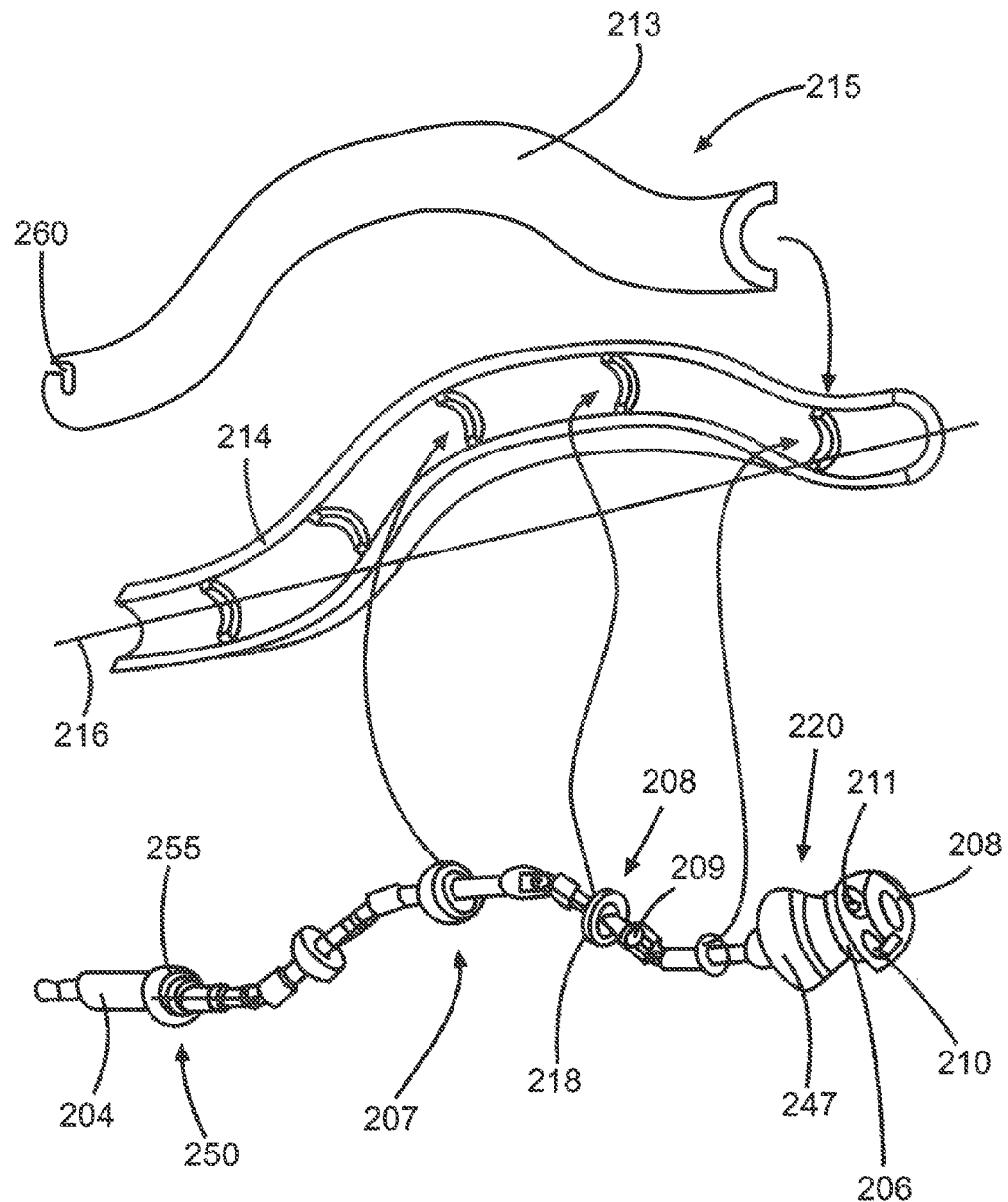
FIG. 6 is an exploded assembly of an alternative embodiment of the present invention.

Referring now to FIG. 6, an alternative embodiment is shown. Similar to FIGS. 1-3 and 5, the reamer spindle 215 has a drive fitting 204, which is adapted to be joined to a rotary power source used to drive the shaft 207 of the reamer spindle 215. The drive shaft 207 can be selected from a variety of current torque transmitting mechanisms or devices including a Nickel Titanium shaft, a flexible round or flat wire wound cable, a series of gear driven shafts, or a series of linkages 208 interconnected by universal joints 209. The drive shaft 207 can also be selected from any torque transmission mechanism or device deemed appropriate for the application. In this embodiment, the shaft 207 is constructed from a series of linkages 208 containing universal joints 209 and bearing members 218 which rest against collars 218' in the housing members 213, 214.

The reamer holding mechanism 220 is preferably a bayonet fitting with a slide 206 carrying a pin component 211 of the reamer holding mechanism 220. The pin 211 works cooperatively with the catch 210 located in the head 208 to form the bayonet for capturing different size reamers while allowing their easy release for size interchangeability and cleaning. The drive shaft 207 is set in housing members 213 and 214, which are separable for cleaning.

Figure 7:
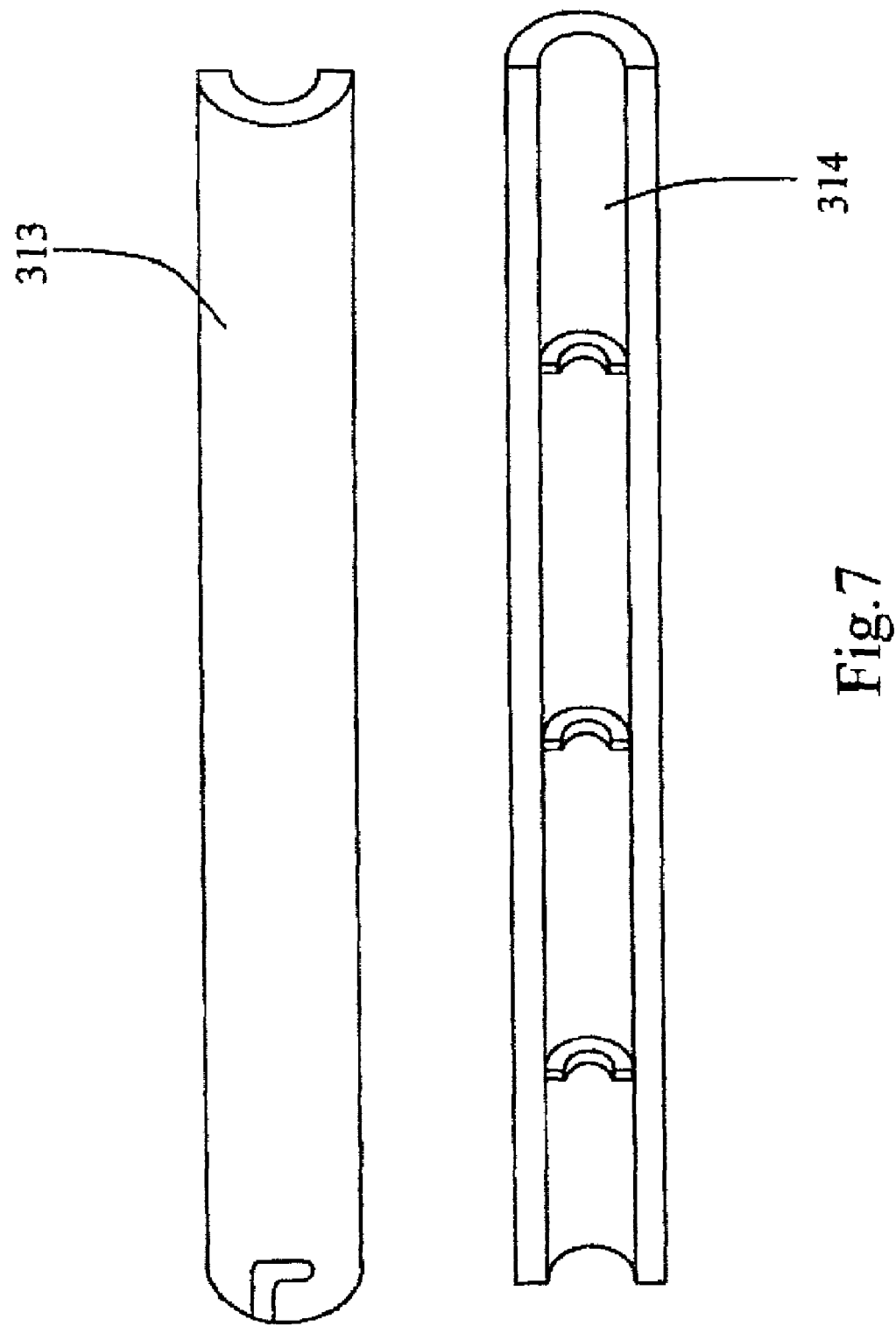
FIG. 7 is an alternative shape housing of the alternative embodiment shown in FIG. 6

There are many ways of connecting the housing members 213 and 214 together. For example, the shaft 207 can include a capture mechanism 247 which is adapted to receive the front ends of the housing members 213 and 214 aligning each with one another and encapsulating the drive shaft 107 to protect the patient's skin from contacting the torque transmitting shaft 207 during operation. Once the housing members 213 and 214 are aligned, a locking mechanism 250 comprised of a ring 255 and a catch 260, which is located in the housing member 213, interact with one another to retain the housing members 213 and 214 in a closed fashion. As with the embodiment described in FIGS. 1-3, and 5, it is preferable to have the drive end 204 substantially collinear with the holding mechanism 220 along axis 216. The housing members 213 and 214 are shown preferably in a bent configuration; however, the reamer spindle 215 with a separable housing includes the option of a straight configuration, as is the case with housing members 313 and 314, shown in FIG. 7, having no bend.

Referring now to FIG. 8, in another embodiment, the drive end 404 of the reamer spindle 315 is situated along an axis 416 parallel and offset to axis 416*a*. Further, a repositionable handle 500 doubles as a component of the capture mechanism 447 in order to hold the two housing members 413 and 414 together.

The capture mechanism 447 slides over the front ends 448 of the housing members 413 and 414, aligning each with one another and thus encapsulating the drive shaft 107 in order to protect the patient's skin from contacting the torque transmitting shaft 107 after being assembled.

Figure 9A:
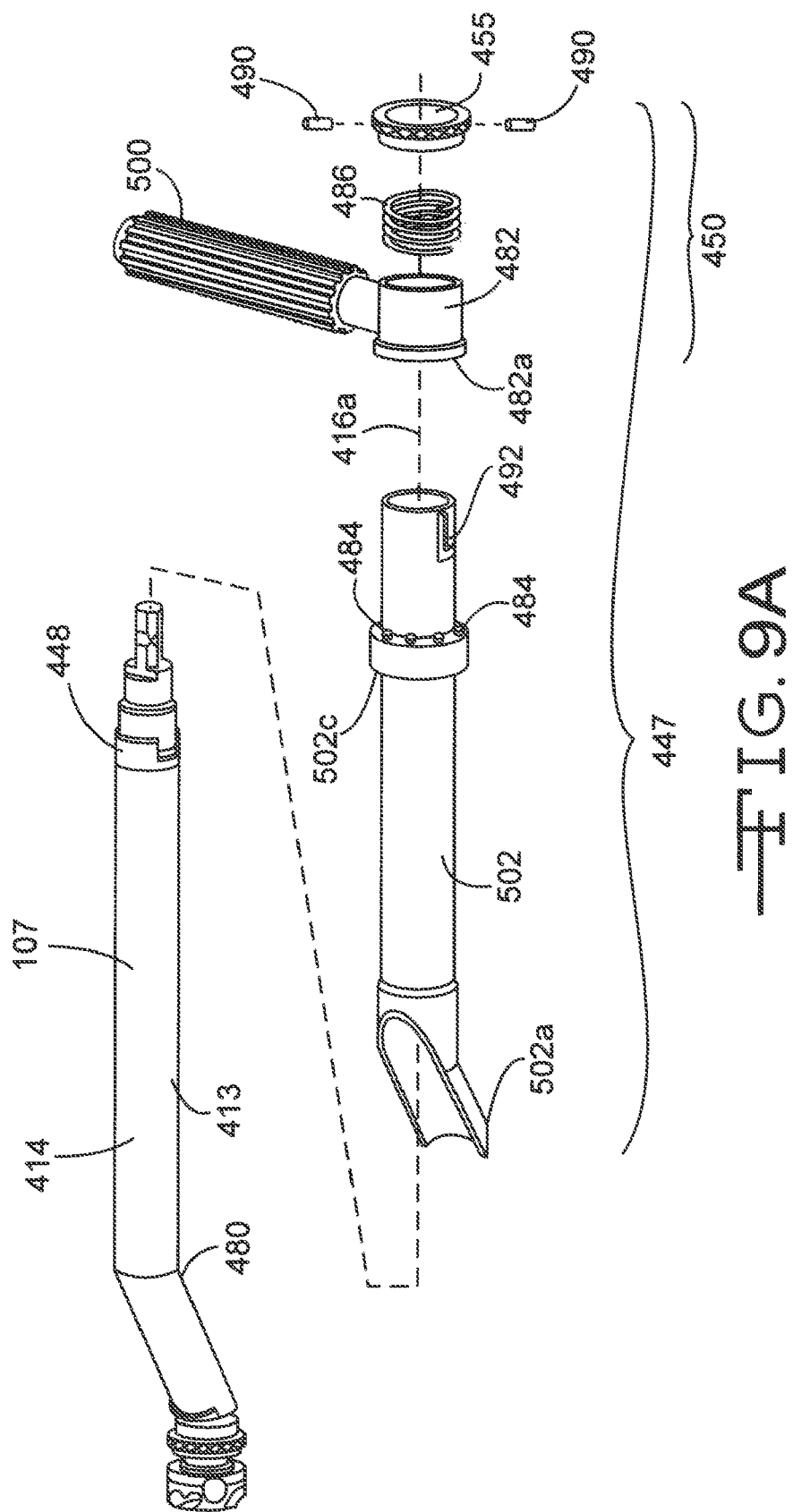
FIG. 9A is an exploded view of the alternate embodiment of FIG. 8.
Figure 9B:
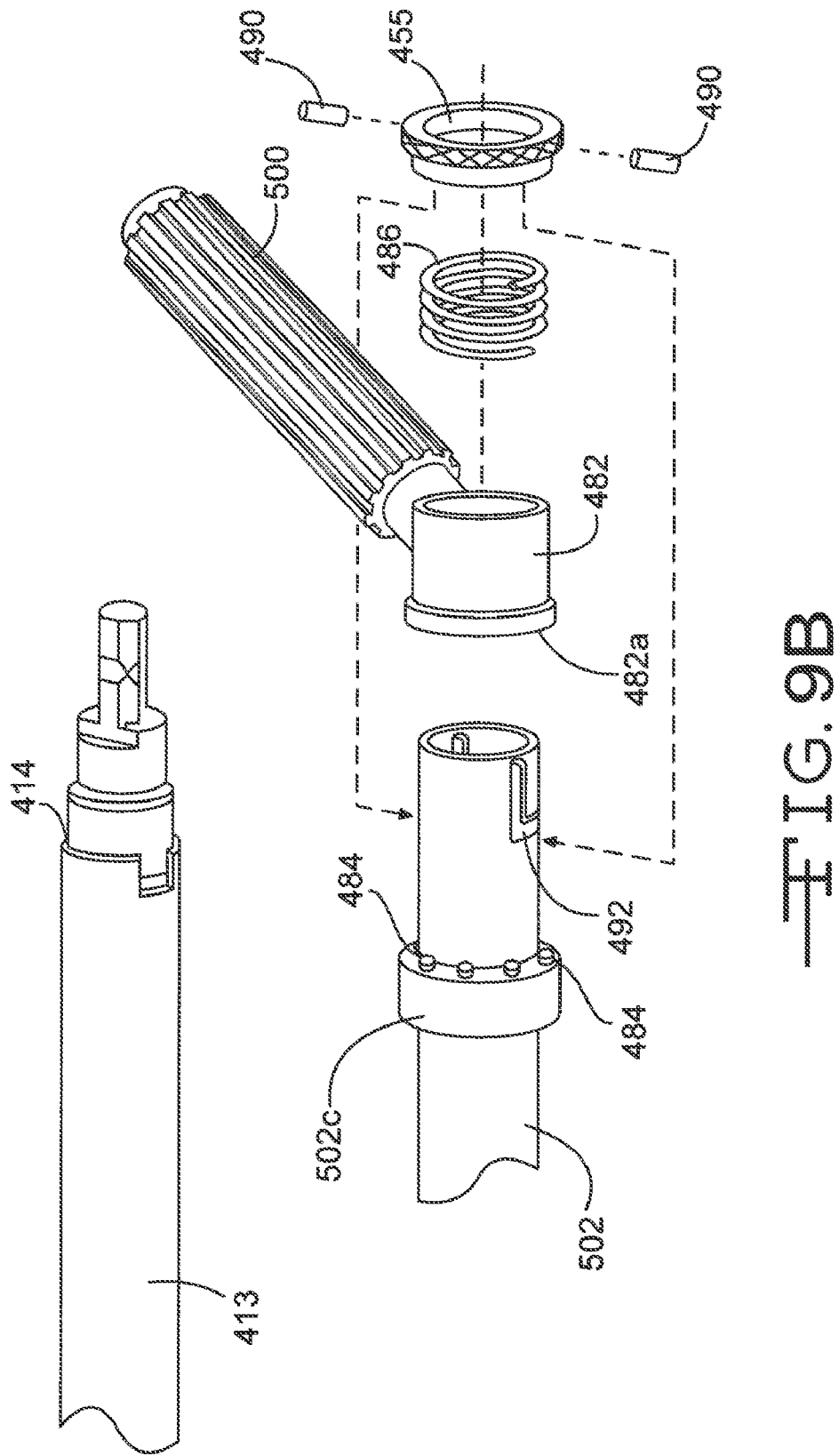
FIG. 9B is a close up of a portion of the exploded view of the alternate embodiment of FIG. 8.
Figure 9C:
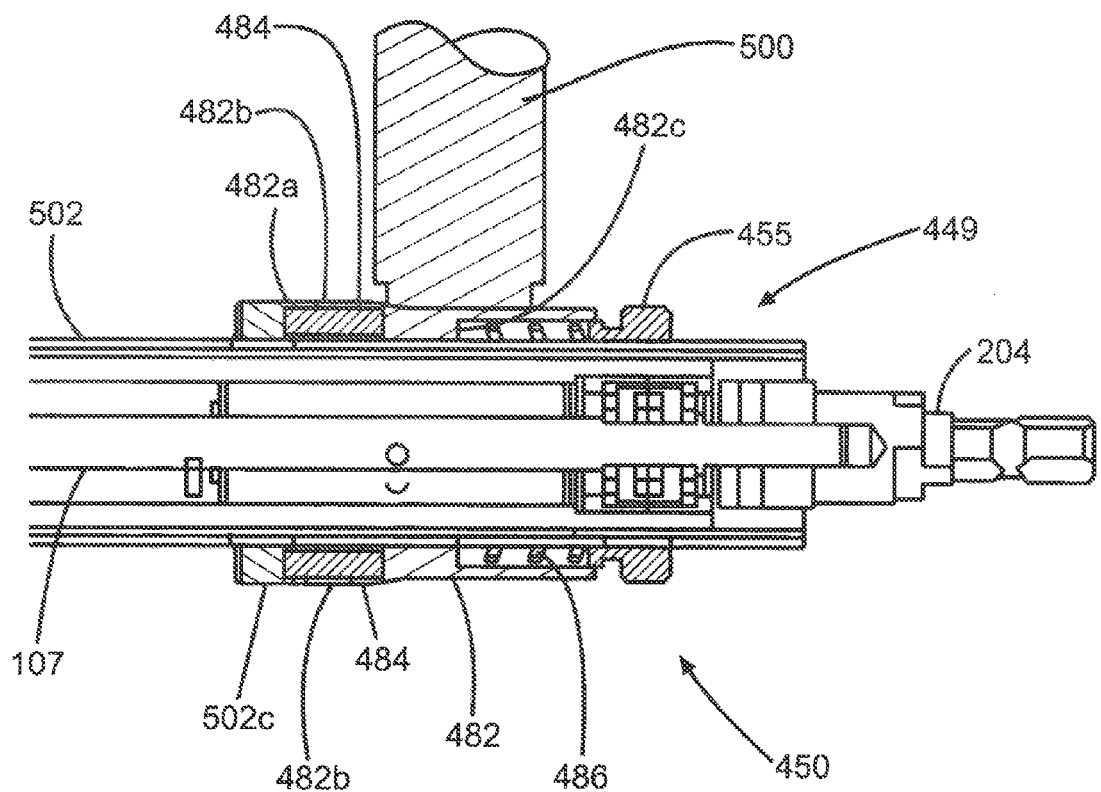
FIG. 9C is a cross-sectional view of the adjustable handle portion of the alternate embodiment of FIG. 8.
Figure 10:
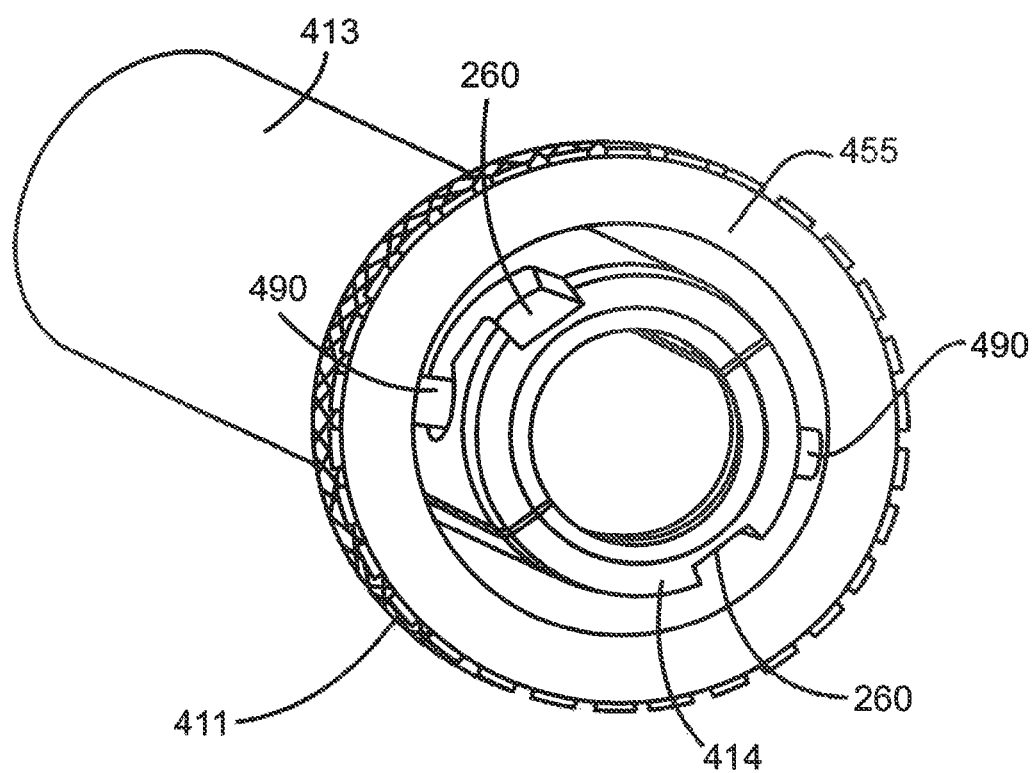
FIG. 10 is a perspective view of key components of the alternate embodiment of FIG. 8.

FIGS. 9A, 9B and 9C more clearly show how the housing members 413 and 414 are aligned and locked in place. The housing members 413 and 414 are oriented with respect to each other when a locking sleeve 502 (having an internal diameter larger than the outside diameter of the housing members) slides over them, abutting against a bend 480 in the housing members. Thin, annular Teflon sleeves (not shown) are disposed between the housing members 413 and 414 and the locking sleeve 502 to facilitate disassembly. A forward mouth section 502*a* of the locking sleeve 502 cradles the bend 480 of the housing members 413 and 414 so as to prevent relative rotation of the locking sleeve and housing members. At the front end 449, the capture mechanism 447 has a locking device 450 which includes an annular sleeve 482 onto which the handle 500 is affixed. The annular sleeve 482 includes a face 482*a* having recesses 482*b* (shown in FIG. 9C) into which pins 484, fixed to a shoulder 502*c* of the locking sleeve 502, are received in order to torsionally rigidly hold the handle 500 in any one of eight positions, according to the preference of the surgeon. A spring 486 biases the annular sleeve 482 into engagement with the pins 484 via, on the one hand, applying spring pressure against an internal shoulder 482*c* (shown in FIG. 9C) in the annular sleeve 482 and, on the other hand, reacting against a locking ring 455. The locking ring 455 includes pins 490 which are affixed thereto and which enter into bayonet slots 492 in the locking sleeve 502 in order to hold the locking device 450 on the end of the locking sleeve and thus the capture mechanism 447 together. The housing members 413 and 414 are held together via the pins 490 which engage the bayonet slots 492*a* in each of the housing members 413 and 414 (best shown in FIG. 10 in which the annular sleeve 482, the spring 486 and the locking sleeve 502 are removed for clarity). The pins 490 of the locking ring 455 and a catch 260 interact with one another to retain the housing members 413 and 414 in a closed fashion while concurrently biasing the spring 486 so as to engage the annular sleeve 482*a* (and thus the handle 500) with the pins 484. Further, sufficient play in the axial movement of the annular sleeve 482 is permitted to enable the surgeon to selectively disengage the sleeve from the pins 484 so as to reposition the handle about the locking sleeve 502 in any one of the eight angular positions of the handle 500, while avoiding disassembly of the spindle 315.

Figure 11:
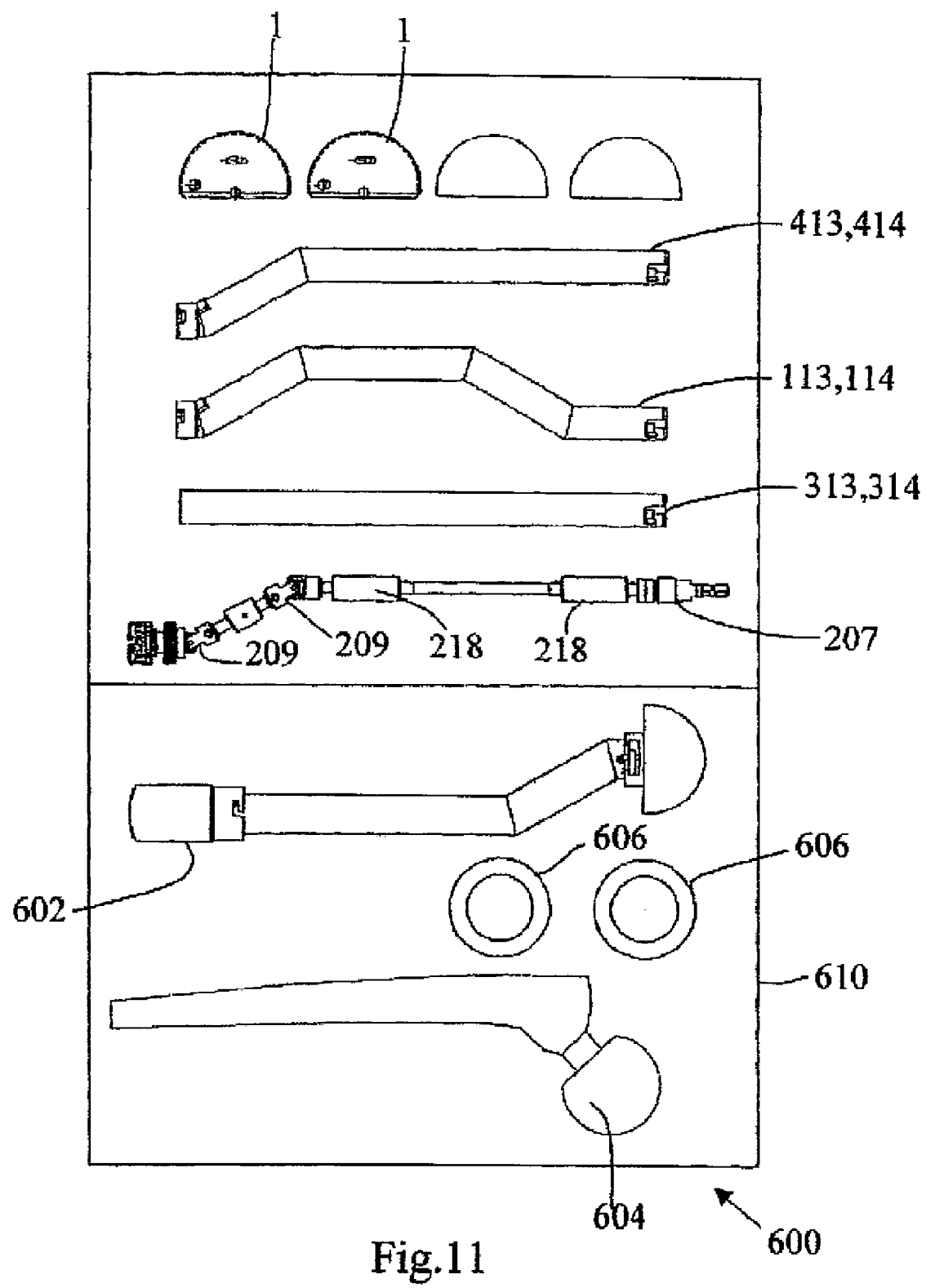
FIG. 11 is a plan view of a surgical reamer kit of the invention.

Referring now to FIG. 11, collectively, these different types of housing members 213-214, 313-314, and 413-414 can be offered as a kit 600 having a selection of different sized reamer housings 113 together with an impactor 602, acetabular implants (not shown), femoral hip prostheses 604, and acetabular cup prostheses (606), the selection of different reamer housing configurations allowing the surgeon to select between a bent, offset configuration or a straight configuration of the reamer spindle 115, 215, and 315 depending on the surgeons approach, which may vary during the same operation or between different patients.

Multiple variations and modifications are possible in the embodiments of the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A surgical tool spindle for containing a drive shaft, the drive shaft being connectable to a rotary drive source and to a surgical rotary cutting tool, the tool handle comprising:
   a) a hollow elongated housing formed of at least two housing members, the housing members together having a drive end portion with a first axis and a front end portion with a second axis parallel to the first axis, the drive end portion and the front end portion of the housing members being connected by an offset and being separable from one another to provide for installing and removing a drive shaft from being housed therein,
      wherein the front end portion of the housing is adapted to mount a driven end attachment assembly of a drive shaft, and the drive end portion of the housing is adapted to mount a driving end attachment assembly of a drive shaft; and
   b) a capture mechanism adapted to receive and hold the housing member and a housed drive shaft together in an operative configuration.

2. The tool handle of claim 1 wherein the offset is proximate the drive end portion of the housing.

3. A surgical tool handle for containing a drive shaft, the drive shaft being connectable to a rotary drive source and to a surgical rotary cutting tool, the tool handle comprising:
   a) a hollow elongated housing having at least two members which together form a first drive end portion with a first axis and a second front end portion with a second axis, the first and second axes being parallel to each other, wherein the drive end portion and the front end portion of the housing members are connected by an intermediate offset as a fixed curved portion that is located more proximate the drive end portion than the first end portion and wherein the drive end and first end portions are separable from one another to provide for installing and removing a drive shaft from being housed therein;
   b) the front end portion being adapted to mount a driven end attachment assembly of the drive shaft for connection to a rotary drive source, and the drive end portion being adapted to mount a driving end attachment assembly of a drive shaft for selectively engaging and disengaging a cutting tool; and
   c) a capture mechanism adapted to receive and hold the housing members and a contained drive shaft together in an operative configuration.

4. The tool handle of claim 3 wherein the second front end portion of the housing is adapted to communicate with the capture mechanism via a locking device.

5. The tool handle of claim 3 wherein the capture mechanism comprises a locking sleeve adapted to slide over the front end portion of the housing and wherein the locking sleeve has a mouth section adapted to abut against and cradle the offset portion of the housing in a manner to prevent rotation of the locking sleeve relative to the housing.

6. The tool handle of claim 5, wherein the locking sleeve has a front sleeve end on which is mounted a locking device, the locking device comprising an annular sleeve which is slidably receivable on the sleeve front end and to which a handle is affixed, the annular sleeve having a face with pin receiving recesses into which pins fixed to a shoulder of the locking sleeve are received to enable the handle to be rotated and selectively fixable in a radial position relative to the second axis.

7. The tool handle of claim 6 wherein the locking device comprises:
   a) a locking ring comprising bayonet pins which limit travel of the locking ring along bayonet slots provided in the front sleeve end of the locking sleeve;
   b) a spring disposed between the annular sleeve and the locking ring to bias the locking ring and the annular sleeve apart when the bayonet pins are set in the bayonet slots so as to compress the spring; and
   c) wherein the front end portion of the assembled housing members is receivable in the locking ring and comprises pin catches engageable by the bayonet pins of the locking ring to hold the housing members and contained drive shaft together in an operative configuration, and wherein unsetting the bayonet pins and release of the bias force against the locking ring enables disassembly of the tool handle to facilitate cleaning and sterilization.

8. The tool handle of claim 6 wherein the annular sleeve comprises a face having recesses set into it for receiving sleeve pins projecting from a sleeve shoulder fixed to the locking sleeve, wherein when the sleeve pins are received into the recesses of the annular sleeve, the annular sleeve is locked to the sleeve shoulder, thereby securing the radial position of the handle relative to the second axis of the housing.

9. The tool handle of claim 5 wherein the drive train is selected from the group consisting of nickel titanium drive trains, ferrous metal drive trains, flexible round wound cable drive trains, flat wire wound cable drive trains, gear-driven shaft drive trains, and drive trains having shafts connected via universal joints.

10. A surgical tool spindle for containing a drive shaft, the drive shaft being connectable to a rotary drive source and to a surgical rotary cutting tool, the tool handle comprising:
   a) a hollow elongated housing formed of at least two housing members, the housing members together having a drive end portion with a first axis and a front end portion with a second axis parallel to the first axis, the drive end portion and the front end portion of the housing members being connected by an intermediate offset and being separable from one another to provide for installing and removing a drive shaft from being housed therein; and
   b) a capture mechanism adapted to receive and hold the housing members and a housed drive shaft together in an operative configuration.

11. The tool handle of claim 3 wherein the offset is a fixed curved portion disposed proximate the drive end portion of the housing.

12. A tool handle, which comprises:
   a) a housing comprising a proximal housing portion extending along a first longitudinal axis to a housing bend portion deviating from the first longitudinal axis thereof to a distal housing portion extending along a second longitudinal axis parallel to the first longitudinal axis, wherein the housing comprises at least a first and a second housing parts; and
   b) a locking sleeve comprising a sleeve sidewall extending from a proximal sleeve portion having a proximal sleeve end to a distal mouth portion, wherein the locking sleeve encloses the housing from the proximal housing portion to the sleeve mouth portion cradling the housing bend portion to prevent rotation of the first and second housing parts relative to the locking sleeve.

13. The tool handle of claim 12 wherein the housing bend portion deviates from the longitudinal axis at an acute angle to the distal housing portion.

14. The tool handle of claim 12 wherein a proximal locking ring supported on the locking sleeve has at least one proximal locking ring pin aligned perpendicular to the first longitudinal axis and sized to travel along a locking sleeve bayonet slot provided in the locking sleeve sidewall, wherein with the housing received in the locking sleeve having the sleeve mouth portion cradling the housing bend portion, the proximal locking ring is manipulatable to move the proximal locking ring pin along the locking sleeve bayonet slot to thereby retain the first and second housing parts contacting each other, and wherein the proximal locking ring is manipulatable to cause the proximal locking ring pin to travel in a reverse direction along the locking sleeve bayonet slot to thereby permit axial movement of the locking sleeve with respect to the housing to separate them from each other for subsequent separation of the first and second housing parts from their contact relationship.

15. The tool handle of claim 14 wherein the locking sleeve bayonet slot provided through the sleeve sidewall is spaced distally from the proximal sleeve end.

16. The tool handle of claim 12 wherein the locking sleeve has two locking sleeve bayonet slots through the sleeve sidewall, the locking sleeve bayonet slots being aligned diametrically opposite each other and wherein the first and second housing parts each comprise proximal housing bayonet slots extending distally from respective proximal ends thereof.

17. The tool handle of claim 16 wherein the proximal locking ring has two proximal locking ring pins oriented perpendicular to the first longitudinal axis and aligned diametrically opposite each other and wherein with the locking sleeve enclosing the housing from the proximal housing portion to the sleeve mouth portion cradling the housing bend portion, the proximal locking ring pins are sized to travel along the respective locking sleeve bayonet slots aligned with the proximal housing bayonet slots provided in the respective first and second housing parts so that the proximal locking ring is manipulatable to move the proximal locking ring pins along both the locking sleeve bayonet slots and the proximal housing bayonet slots to retain the first and second housing parts contacting each other.

* * * * *